US007510735B2

(12) United States Patent
Shimakawa et al.

(10) Patent No.: US 7,510,735 B2
(45) Date of Patent: Mar. 31, 2009

(54) METHOD OF EVALUATING THE EXTENT OF REACHING THE INTESTINE OF BIFIDOBACTERIUM IN FERMENTED MILK FOOD OR DRINK

(75) Inventors: Yasuhisa Shimakawa, Tokyo (JP); Masaki Serata, Tokyo (JP); Hirokazu Tsuji, Tokyo (JP); Koichiro Sonoike, Tokyo (JP); Akimitsu Takagi, Tokyo (JP); Mika Miura, Tokyo (JP); Fumiyasu Ishikawa, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 709 days.

(21) Appl. No.: 10/470,776

(22) PCT Filed: Dec. 21, 2001

(86) PCT No.: PCT/JP01/11266

§ 371 (c)(1), (2), (4) Date: Jul. 31, 2003

(87) PCT Pub. No.: WO02/061118

PCT Pub. Date: Aug. 8, 2002

(65) Prior Publication Data

US 2004/0052902 A1 Mar. 18, 2004

(30) Foreign Application Priority Data

Feb. 1, 2001 (JP) ............................ 2001-025297

(51) Int. Cl.
*A23C 9/12* (2006.01)
*A23C 17/00* (2006.01)

(52) U.S. Cl. ............................................ 426/42; 435/4

(58) Field of Classification Search .................. 426/34, 426/42; 435/4
See application file for complete search history.

(56) References Cited

U.S. PATENT DOCUMENTS

| | | | | |
|---|---|---|---|---|
| 4,187,321 | A * | 2/1980 | Mutai et al. | 426/43 |
| 4,588,595 | A * | 5/1986 | Okonogi et al. | 435/252.4 |
| 5,711,977 | A | 1/1998 | Yang et al. | |

FOREIGN PATENT DOCUMENTS

| | | |
|---|---|---|
| JP | 1-257476 | 10/1989 |
| WO | 99/11755 | 3/1999 |

OTHER PUBLICATIONS

International Journal of Food Microbiology, vol. 47, pp. 25-32 1999.
Journal of Dairy Science, vol. 82, No. 1, pp. 23-31 1999.
P. Marteau, et al., Journal of Dairy Science, vol. 80, No. 6, XP-002268667, pp. 1031-1037,"Survival of Lactic Acid Bacteria in a Dynamic Model of the Stomach and Small Intestine: Validation and the Effects of Bile", 1997.
W. Sun, et al., international Journal of Food Microbiology, vol. 61, No. 1, XP-002268665, pp. 17-25, "Survival of Bifidobacteria in Yogurt and Simulated Gastric Juice Following Immobilization in Gellan-Xanthan Beads", Oct. 1, 2000.
W. P. Charteris, et al., Journal of Food Protection, vol. 63, No. 10, XP-001104895, pp. 1369-1376, "Effect of Conjugated Bile Salts on Antibiotic Susceptibility of Bile-Salt-Tolerant Lactobacillus and Bifidobacterium Isolates", Oct. 2000.
S. K. Lee, et al., Letters in Applied Microbiology, vol. 28, No. 2, XP-002268669, pp. 153-156, "The Viability of Bifidobacteria Introduced Into Kimchi", Feb. 1999.

* cited by examiner

*Primary Examiner*—Keith D Hendricks
*Assistant Examiner*—Jyoti Chawla
(74) *Attorney, Agent, or Firm*—Oblon, Spivak, McClelland, Maier & Neustadt, P.C.

(57) ABSTRACT

A *Bifidobacterium* that is resistant to acid and bile and which retains at least 20% viability after acid and bile treatment. Foods and drinks containing an acid- and bile-resistant *Bifidobacterium*. Methods for providing viable *Bifidobacteria* to the intestine after ingestion of a food or drink containing an acid- and bile-resistant *Bifidobacterium*.

9 Claims, No Drawings

METHOD OF EVALUATING THE EXTENT OF REACHING THE INTESTINE OF BIFIDOBACTERIUM IN FERMENTED MILK FOOD OR DRINK

This application is a national-stage filing under 35 U.S.C. §371 of PCT/JP01/11266, filed Dec. 21, 2001. It also claims priority to JAPAN 2001-25297, filed Feb. 1, 2001.

TECHNICAL FIELD

The present invention relates a convenient method for assessing the extent to which *Bifidobacterium* bacteria in a fermented milk food or drink reach the intestines when the food or drink is administered orally to human beings; and *Bifidobacterium* bacteria having a high viability when assessed by the method.

BACKGROUND ART

*Bifidobacterium* bacteria are reported to exhibit various physiological effects such as inhibitory effects against harmful intestinal bacteria, intestinal function controlling effects and immunoactivating effects. A number of products containing *Bifidobacterium* bacteria have been put on the market, for example, in the form of fermented milk products or live-bacteria-containing preparations, and they have established a firm position in the market. In particular, a strong preference to fermented milk food and drink enables continuous intake of *Bifidobacterium* bacteria and they are therefore a suitable form for administration.

*Bifidobacterium* bacteria exhibit most of their physiological effects by producing acetic acid or the like as a metabolite after reaching the intestines. In order to produce satisfactory effects, they must reach the intestines in the viable form. The extent to which bacteria reach the intestines has conventionally been judged with their recovery rate from feces as an index. Described specifically, the number of living bacteria in the feces reflects the extent to which the bacteria reach the intestines so that the extent has been confirmed by collecting the feces of the human beings to which the bacteria were administered and counting the number of living bacteria (collection rate) in the feces.

It is generally considered that *Bifidobacterium* bacteria have difficulty in reaching the intestinal tracts because of weak tolerance to an acid and bile. In other words, when they are taken orally, there is a possibility of them being killed by gastric juice or bile prior to reaching the intestines.

In recent years, improvement of various production techniques enables an increase in the very number of bacteria which can be administered so that even if some of the bacteria are killed, physiological effects can still be expected from the remaining ones. Upon production of fermented foods containing *Bifidobacterium* bacteria, a variety of components for improving bacterial viability during storage, for example, N-acetyl glucosamine, pantothenic acid, peptides and lactulose are added. Their action is considered to heighten the extent to which *Bifidobacterium* bacteria reach the intestines after their administration.

In order to attain stronger physiological effects, a greater number of viable bacteria must be caused to reach the intestines. There is accordingly a demand for improving the extent to which the bacteria reaching the intestines. An administration test to human beings becomes inevitable for finding the extent, that is, a recovery ratio of them from feces. Cumbersome and long-term works necessary for the test have however hampered the implementation of such a test.

There are some reports on the production of a strain endowed in advance with tolerance to gastric juice or bile which will otherwise be a barrier against the orally taken bacteria. For example, it is described in Japanese Patent Laid-Open No. Hei 9-322762 that use of *Bifidobacterium* bacteria exhibiting high tolerance to acids, bile salt and oxygen enables culture on skim milk or the like under aerobic conditions without adding a growth promoting substance. In *International Journal of Food Microbiology,* 47, 25-32(1999), described are two strains of *Bifidobacterium* bacteria having high tolerance to an acid and bile.

Considering the possibility of improving the extent to which bacteria reach the intestines upon their administration by the use of such highly tolerant bacteria, the present inventors created such a strain having high tolerance to an acid and bile, prepared a syrup-containing fermented milk food or drink by using the strain, administered it to human beings and found a recover ratio from feces. As a result, it has been revealed that there is not always a correlation between the tolerance and the recovery ratio.

Accordingly, an object of the present invention is to construct a convenient and accurate assessing system which reflects the extent to which *Bifidobacterium* bacteria in a fermented milk food or drink reach the intestines. Another object of the present invention is to create a strain superior in the extent to the conventional *Bifidobacterium* bacteria and provide a *Bifidobacterium*-bacteria-containing fermented milk food or drink by using the bacteria.

DISCLOSURE OF THE INVENTION

The present inventors carried out an investigation on a recovery ratio of *Bifidobacterium* bacteria from feces of persons to whom a *Bifidobacterium*-bacteria-containing fermented milk food or drink had been administered. As a result, it has been found that in a fermented milk food or drink, particularly, a syrup-containing fermented milk food or drink, a recovery ratio is relatively high just after the preparation, but it shows a drastic reduction after about one week from the preparation. When the distribution of fermented milk food and drink is taken into consideration, a sufficiently high recovery ratio must be kept even after storage for such a period. The present inventors have carried out a further investigation using a *Bifidobacterium*-bacteria- and syrup-containing fermented milk food or drink stored for about one week. As a result, it has been found that the extent to which *Bifidobacterium* bacteria in a fermented milk food or drink reach the intestines when the food or drink is orally administered can be assessed conveniently and accurately by measuring bacterial viability after successive treatments with an acid and bile. It has also been found that when a fermented milk or food containing a strain which exhibits at least predetermined bacterial viability, with the bacterial viability after successive treatments with an acid and bile as an index, is administered, the extent to which bacteria reach the intestines is excellent even about one week after the preparation of the food or drink, leading to completion of the invention.

In one aspect of the present invention, there is thus provided a method for assessing the extent to which *Bifidobacterium* bacteria in a *Bifidobacterium*-bacteria-containing fermented milk food or drink reach the intestines when the fermented food or milk is orally administered to human beings, which comprises successively treating the fermented milk food or drink with an acid and then bile; and measuring bacterial viability after these treatments.

In another aspect of the present invention, there are also provided *Bifidobacterium* bacteria exhibiting at least 20% of bacterial viability as measured by the above-described assessing method; and a *Bifidobacterium*-bacteria-containing fermented milk food or drink, which comprises the above-described bacteria.

BEST MODE FOR CARRYING OUT THE INVENTION

Any *Bifidobacterium*-bacteria-containing fermented milk food or drink is usable for the assessment in the present invention. Examples include fermented milk food and drink each obtained by adding a syrup to a fermented milk prepared by culturing *Bifidobacterium* bacteria on a nutrient medium such as GAM medium (product of Nissui Pharmaceutical) and then culturing the resulting bacteria as a seed on a milk medium. In particular, the extent to which *Bifidobacterium* bacteria in a syrup-containing fermented milk food or drink reaches the intestines lowers during storage so that the assessing method of the present invention exhibits effectiveness for syrup-containing fermented milk products. The term "milk" as used herein 4means cow milk (whole milk), skim milk which is a processed product thereof, milk of another animal such as goat, sheep or the like, and soy milk which is of plant origin. Examples of the syrup include saccharides such as glucose, sucrose, fructose-glucose syrup, glucose-fructose syrup and comb honey; and sugar alcohols such as sorbitol, xylitol, erythritol, lactitol, and palatinit. The content of the syrup is preferably 0.1 to 10 wt. %. The fermented milk food or drink preferably contains $1\times10^7$ to $5\times10^9$ cfu/mL, particularly preferably $1\times10^8$ to $1\times10^9$ cfu/mL of *Bifidobacterium* bacteria. The number of bacteria exceeding $5\times10^9$ disturbs accurate judgement, because the burden of an acid or bile is insufficient for such a count. On the other hand, the number of bacteria less than $1\times10^7$ is inappropriate, because the burden of an acid or bile on each bacteria is excessively large.

In the fermented milk food or drink, an emulsifier such as sucrose fatty acid ester, polyglycerin fatty acid ester or lecithin, and a thickener (stabilizer) such as agar, gelatin, carrageenan, guar gum, xanthan gum, pectin or locust bean gum can be incorporated. Vitamins such as vitamin A, B-vitamins, vitamin C and vitamin E, and herb extracts can also be incorporated.

Microorganisms other than *Bifidobacterium* bacteria can be used in combination therewith for the preparation of a fermented milk food or drink. Preferred examples of microorganisms include *Lactobacillus* bacteria such as *Lactobacillus acidophilus, Lactobacillus gasseri, Lactobacillus plantarum, Lactobacillus buchneri, Lactobacillus casei, Lactobacillus johnsonii, Lactobacillus gallinarum, Lactobacillus amylovorus, Lactobacillus brevis, Lactobacillus rhamnosus, Lactobacillus kefir, Lactobacillus paracasei, Lactobacillus crispatus* and *Lactobacillus delbrueckii* subsp. *delbrueckii; Streptococcus* bacteria such as *Streptococcus thermophilus; Lactococcus* bacteria such as *Lactococcus lactis* subsp. *lactis; Bacillus* bacteria such as *Bacillus subtilis*; and yeasts belonging to the genera *Saccharomyces, Torulaspora* and *Candida* such as *Saccharomyces cerevisiae, Torulaspora delbrueckii* and *Candida kefir.*

A fermented milk food or drink prepared using, in combination with *Bifidobacterium* bacteria, at least one lactic acid bacteria selected from the above-described *Lactobacillus, Streptococcus* and *Lactococcus* bacteria is preferred, because owing to a high preference to such a drink, it facilitates continuous administration and in addition, it is highly effective for improving the intestinal reaching degree or recovery ratio.

The fermented milk food or drink may be prepared in a manner known per se in the art. For example, a fermented milk base is prepared by inoculating and culturing *Bifidobacterium* bacteria singly or simultaneously with lactic acid bacteria on a sterilized milk medium, and then homogenizing the cultured bacteria. To the resulting fermented milk base is added a syrup solution which has been prepared separately. After mixing, the mixture is homogenized in a homogenizer, followed by the addition of a flavor, whereby a final product is prepared.

The fermented milk food or drink thus available can be provided in any one of soft type, fruits flavor type, solid form and liquid form.

The fermented milk food or drink to be subjected to successive treatments with an acid and bile is preferably that which has been stored at low temperatures for 7 days after completion of the incubation, with the storage starting day reckoned as 0 (in the case of a syrup-containing fermented milk food or drink, with the day on which the syrup and *Bifidobacterium* bacteria were added reckoned as 0). It has preferably a pH of from 5.0 to 5.8.

Although no particular limitation is imposed on the strain of the *Bifidobacterium* bacteria to be employed, those derived from human beings are preferred. Preferred are *Bifidobacterium breve, Bifidobacterium bifidum, Bifidobacterium longum, Bifidobacterium infantis, Bifidobacterium adolescentis, Bifidobacterium catenulatum* and *Bifidobacterium pseudocatenulatum*, of which *Bifidobacterium breve, Bifidobacterium bifidum* and, *Bifidobacterium iongum* are particularly preferred.

The term "successive treatments with an acid and bile" as used herein means treatment of the fermented milk food or drink with an acid, followed by treatment with bile. The term "successive treatments" as used herein means that the treatment with bile is performed instantly after the treatment with an acid or performed without recovering the activity of bacteria. The term "without recovering the activity of bacteria" means that no positive treatment is given for recovering the activity of bacteria, for example, addition of a neutralizer to the acid treated solution or dilution with a buffer or medium.

The term "acid treatment" as used herein means treatment of adding the fermented milk food or drink to a solution, which has been made more acidic than the optimum pH of *Bifidobacterium* bacteria by the addition of an organic acid such as acetic acid, lactic acid, citric acid, malic acid, succinic acid, butyric acid or propionic acid, or an inorganic acid such as hydrochloric acid, sulfuric acid, nitric acid or phosphoric acid, thereby causing damage to the food. Although no particular limitation is imposed on the acid to be employed, use of an organic acid is preferred, because existence of a salt adversely affects the growth of some strains of *Bifidobacterium* bacteria and this influence cannot always be neglected when a correlation between bacterial viability and a recovery ratio is considered. Use of acetic acid, lactic acid or hydrochloric acid heightens a correlation between bacterial viability and the extent to which bacteria reach the intestines and is therefore particularly preferred.

The acid containing solution to be used for the acid treatment is preferably adjusted at pH of from about 3.0 to 5.5, especially preferably from about 4.0 to 4.5. When the pH exceeds 5.5, it becomes, in most cases, higher than that of popular fermented milk products themselves and can cause only a slight damage to the *Bifidobacterium* bacteria. At pH less than 3.0, on the other hand, most of the bacteria will be killed by such a strong acid solution within an extremely short time. Thus, at pH outside the above-described range, a difference between strains in the bacterial viability after the treatment cannot be detected.

After the addition of the fermented milk food or drink to the acid-containing solution, the resulting mixture may be treated for about 1 to 60 minutes at a temperature suited for the growth of *Bifidobacterium* bacteria, that is, about 30 to 42° C. Treatment at about 36 to 38° C. for about 10 to 30 minutes is preferred, for such conditions reflect the living conditions of the bacteria and are convenient for the implementation of the test.

In the present invention, the fermented milk food or drink after the acid treatment is treated with bile. Described specifically, the fermented milk food or drink after the acid treatment is added directly to a bile solution. Although no particular limitation is imposed on the conditions of the treatment with bile, it is recommended to add the acid-treated fermented milk food or drink to a solution obtained by adding sodium phosphate as a neutralizer to about 0.1 to 5% of bile or bile salt, and treat the mixture at 30 to 42° C. for about 1 to 240 minutes. In order to heighten the correlation between the bacterial viability and the extent to which bacteria reach the intestines and clearly differentiate the tolerance between strains, it is preferred to add about 0.5 to 2% of bile or bile salt and treat the mixture at 36 to 38° C. for about 30 to 60 minutes.

More preferable successive treatments with an acid and bile are treatments of a fermented milk food or drink, which contains *Bifidobacterium* bacteria (the original number of bacteria: about $1\times10^8$) and has been stored for 7 days, with an acid of pH 4.3 at 36 to 38° C. for 10 to 30 minutes and then with 1% bile at 36 to 38° C. for 30 to 60 minutes.

Particularly preferable specific conditions of the successive treatments with an acid and bile are as follows: First, 1 mL of a fermented milk food or drink is added to 10 mL of an acid treatment solution adjusted with acetic acid to pH 4.3 and then, the resulting mixture is treated at 37° C. for 30 minutes. Rightly after the first treatment, 1 mL of the acid treated solution is added to 10 mL of a bile treatment solution containing 1% of bile, followed by treatment therewith at 37° C. for 30 minutes. The treatment under such conditions enables the bacterial viability to roughly coincide with the extent to which bacteria reach the intestines irrespective of the kind of the strains to be assessed. They also make it possible to clearly differentiate the bacterial viability between strains.

The bacterial viability after the successive treatments with an acid and bile can be determined by comparing the number of bacteria in the fermented milk food or drink before the treatments with that after the treatments. In other words, a ratio of the number of bacteria after the treatments to that before the treatments may be calculated. The number of bacteria can be measured in a manner known per se in the art.

The bacterial viability of *Bifidobacterium* bacteria after such successive treatments with an acid and bile shows a close correlation with the extent to which *Bifidobacterium* bacteria in a fermented milk food or drink reach the intestines when the milk or food is orally administered to human beings. Described specifically, the bacterial viability after the successive treatments serves as a parameter which varies depending on the extent to which *Bifidobacterium* bacteria reach the intestines upon oral administration of the fermented milk food or drink to human beings. It is not known exactly but this close correlation is considered to owe to the fact that the stress applied to *Bifidobacterium* bacteria, first by the acid treatment to lower their activity and then by the treatment with bile, is analogous to the stress occurring in the human intestinal tracts.

The term "extent to which bacteria reach the intestines" as used herein means, in the case where a *Bifidobacterium*-bacteria- and syrup-containing fermented milk food or drink is orally administered to human beings, a ratio of the number of the bacteria reaching the intestines to the number of administered bacteria. The number of bacteria reaching the intestines is considered to be almost similar to the number of bacteria recovered from the feces so that in practice, the latter number is regarded as the number of bacteria reaching the intestines.

Even if the bacterial viability is measured after either one of the acid treatment or the bile treatment, no correlation is available between the bacterial viability and the extent to which bacteria reach the intestines or recovery ratio. When the acid treatment and bile treatment are conducted at some interval, or when the bile treatment is followed by the acid treatment, bacterial viability has no correlation with the extent to which bacteria reach the intestines or recovery ratio.

When the conventional *Bifidobacterium* bacteria were employed, for example, for food or drink such as fermented milk product, the extent to which bacteria reach the intestines or recovery ratio of them was sufficient when the product was taken just after preparation, but it lowered when the product was supplied after about one week refrigeration. This tendency was marked in a syrup-containing fermented milk food or drink. The strain which has been confirmed to have high bacterial viability by the assessing method of the present invention is excellent in the extent to which bacteria reach the intestines or recovery ratio even after one week storage in the form of a fermented milk food or drink.

In the present invention, it has been confirmed that a fermented milk food or drink, which has been prepared using a novel strain having bacterial viability of 20% or greater, more preferably, 30% or greater after the successive treatments with an acid and bile, attains a similar level of the extent to which bacteria reach the intestines or recovery ratio to that just after preparation even if it is stored for about 1 week. In spite of the presumption that the higher the number of *Bifidobacterium* bacteria in a fermented milk food or drink, the higher the extent to which the bacteria reach the intestines, the results of the study by the present inventors have revealed that the extent tends to lower when the food is stored for 1 week, resulting in a decrease in the recovery rate from feces.

When a fermented milk food or drink containing at least $1\times\mathbf{10}^8$ cfu/ml of human-derived *Bifidobacterium* bacteria exhibits bacterial viability of 20% or greater after refrigeration for one week, the treatment at 37° C. for 30 minutes with an acid treatment solution adjusted to pH 4.3 with 10 times the weight of acetic acid and then, the treatment at 37° C. for 30 minutes with 10 times the weight of 1% bile acid, the number of bacteria reaching the intestines can be kept at about $1\times10^7$ cfu/g when the food or drink is administered to human beings after one week storage. Fermented milk food and drink equipped with such number of bacteria and bacterial viability are particularly preferred, because if the number of bacteria reaching the intestines can be kept at about $1\times10^7$ cfu/g, proliferation of *Bacteroides* spp. and *Clostridium* spp. bacteria which are called "intestinal bad bacteria" can be controlled.

There is no particular limitation imposed on the strain of *Bifidobacterium* bacteria having high bacterial viability after the successive treatments with an acid and bile, and a high extent to which bacteria reach the intestines or high recovery ratio can be expected from the use of any human-derived strain exemplified above. Among them, *Bifidobacterium breve*, *Bifidobacterium bifidum* and *Bifidobacterium longum* are preferred, because physiological effects and safety for infants or the aged have already been confirmed well.

Strains having high tolerance to such successive treatments with an acid and bile can be produced, for example, by the following process.

To a fermented milk prepared using *Bifidobacterium* bacteria as a parent strain, a syrup is added to prepare a fermented drink. The drink is dispensed into an appropriate container and it is refrigerated. The fermented drink after refrigeration is subjected to acid and bile treatments, followed by centrifugal separation to recover the bacteria. From these bacteria, those having excellent tolerance to successive treatments with an acid and bile are selected.

Although any strain of *Bifidobacterium* bacteria is usable for the above-described method without limitation, but bacteria selected from *Bifidobacterium breve, Bifidobacterium bifidum* and *Bifidobacterium longum* are preferably employed because of the same reasons as described above.

Two strains YIT 4125 and YIT 4126 which have been recognized to have high bacterial viability after the successive treatments with an acid and bile as a result of the above-described method are deposited with International Patent Organism Depositary, National Institute of Advanced Industrial Science and Technology (Chuo 6 1-1-1 Higashi, Tsukuba, Ibaraki, Japan) as of Oct. 27, 2000; the former as *Bifidobacterium breve* YIT 4125 (FERM BP-7813) and the latter as *Bifidobacterium breve* YIT 4126 (FERM BP-7814).

Alternatively, a strain having high bacterial viability after the successive treatments with an acid and bile can be selected by exposing it to ultraviolet rays or treating it with a mutagen such as nitrosoguanidine (NTG) or ethylmethane sulfonate (EMS).

The *Bifidobacterium* bacteria having high bacterial viability after the successive treatments with an acid and bile, which bacteria have been obtained by the above-described method or another method, exhibit a high extent to which bacteria reach the intestines or recovery ratio. The above-described two strains are excellent strains with bacterial viability of 35% or greater after the successive treatments with an acid and bile.

In addition, the present invention relates to *Bifidobacterium*-bacteria- and syrup-containing fermented milk food and drink having high bacterial viability after the successive treatments with an acid and bile. The forms of the fermented milk food and drink are similar to those described above.

EXAMPLES

The present invention will hereinafter be described in further detail by Examples. It should however be borne in mind that the present invention is not limited to or by them.

Referential Example 1

The bacteria obtained by treating the *Bifidobacterium Breve* 4052 strain (*B. breve* A), a parent strain, with N-methyl-N'-nitrosoguanidine (NTG) were cultured on an anaerobic skim milk medium. To 10 mL of an acid treatment solution (pH 3.8) was added 1 mL of the resulting culture solution, followed by treatment at 37° C. for 8 minutes. On an anaerobic skim milk medium, 1% of the resulting solution was inoculated and cultured at 37° C. for 20 hours. After storage of the culture solution at 10° C. for 4 days, 1 mL of the resulting solution was added to 10 mL of an acid treatment solution (pH 3.8), whereby a similar treatment was conducted. The bacteria after the treatment were cultured on a skim milk medium. Several single-colony derived strains were selected from the culture and their acid tolerance was compared. As a result, the *Bifidobacterium breve* N4 strain (*B. breve* B) was selected as a strain having improved acid tolerance. The strain had improved bile tolerance at the same time.

Composition of Anaerobic Skim Milk Medium

| | |
|---|---|
| Skim milk | 12% |
| Yeast extract | 1% |
| Cysteine | 0.03% |
| Calcium carbonate | 2% |

Nitrogen was blown into the medium for 20 minutes, followed by sealing with a rubber stopper and autoclave sterilization at 115° C. for 20 minutes.

Example 1

Three fermented milks were prepared by inoculating seed cultures of *B. breve* A, *B. breve* B (N4 strain) and *B. bifidum* C (YIT 4007 strain) on a 18% whole milk medium (added with 0.03% yeast extract) sterilized at 100° C. for 90 minutes, and culturing at 34° C. for about 20 hours. To each of the fermented milks thus obtained, a glucose-fructose syrup was added to give a final concentration of 8% and the resulting mixtures were used as test samples. These samples were each dispensed in a glass container. After the container was sealed with a rubber stopper to shut off the air flow into the container, it was stored at 10° C. for 7 days.

Recovery of *bifidobacteria* from the feces of human beings administered with these samples was studied. Eighteen healthy adult male volunteers (average age: 33) were divided into three groups at random and they were asked to drink, for 3 days, 100 mL/day of the fermented milk prepared using each strain. On the next day after completion of drinking, feces were recovered from them and diluted stepwise with an anaerobic diluting solution. From the number of colonies appearing on a selective plate, the number of recovered bacteria was calculated. A T-CBPC plate was used for *B. breve* A and B strains, while a T-LCM plate was used for the *B. bifidum* C strain.

Composition of Anaerobic Dilution Water

| | |
|---|---|
| Potassium dihydrogen phosphate | 0.0225% |
| Dipotassium hydrogen phosphate | 0.0225% |
| Sodium chloride | 0.045% |
| Ammonium sulfate | 0.0225% |
| Calcium chloride | 0.00225% |
| Magnesium sulfate | 0.00225% |

After the above-described composition was dissolved in distilled water, nitrogen was brown into the resulting solution to make it anaerobic. With a rubber stopper, air was shut off, followed by autoclave sterilization (121° C. for 15 minutes).

Composition of T-CBPC Plate

| | |
|---|---|
| TOS (product of Yakult) | 1% |
| Trypticase peptone (BBL) | 1% |
| Yeast extract (Difco) | 0.1% |
| Potassium dihydrogen phosphate | 0.3% |
| Dipotassium hydrogen phosphate | 0.45% |
| Ammonium sulfate | 0.3% |

-continued

| | |
|---|---|
| Magnesium sulfate | 0.02% |
| Cysteine hydrochloride | 0.05% |
| Lab-Lemco powder (OXOID) | 0.1% |
| Agar (Difco) | 1.5% |

The above-described composition was dissolved in distilled water, followed by autoclave sterilization at 115° C. for 15 minutes. After cooling to 50° C., Carbenicillin (Sigma) which had been sterile-filtered and Streptomycin sulfate (Sigma) were added to the resulting solution to give final concentrations of 1 μg/mL and 0.5%, respectively. An agar plate was prepared in such a manner.

Preparation of T-LCM Plate

A T-LCM plate was prepared in a similar manner to that employed for the preparation of the above T-CBPC plate except that 2 μg/mL of Lincomycin (Sigma) was added instead of 1 μg/mL of Carbnenicillin (Sigma) as a sterile-filtered antibiotic.

As a result, a difference in recovering property as described below was observed among three fermented milks prepared using three *bifidobacteria* strains.

TABLE 1

| | Strain | | |
|---|---|---|---|
| | A | B | C |
| The initial number of bacteria | $3.99 \times 10^8$ | $3.16 \times 10^8$ | $7.94 \times 10^8$ |
| The number of bacteria recovered | $4.79 \times 10^4$ | $4.37 \times 10^5$ | $9.55 \times 10^6$ |

Example 2

In vitro model system which reflects the recovery property in Example 1 was studied. With preference on convenience, the system permitting completion of treatment within from 30 minutes to 1 hour was studied.

First, tolerance to acid treatment was evaluated as a model of the stomach through which food passes first among digestive tracts. As an acid treatment solution, a solution having a pH lowered by the addition of an acid to a *bifidobacteria* medium was used, with reference to the method of Kobayashi, et al. (*Japanese Journal of Bacteriology,* 29, 691-697 (1974)).

Composition of Acid Treatment Solution

| | |
|---|---|
| Trypticase peptone (BBL) | 1% |
| Yeast extract (Difco) | 0.5% |
| Tryptose (Difco) | 0.3% |
| Sodium chloride | 0.2% |
| Monoammonium citrate | 0.2% |
| Cysteine hydrochloride | 0.05% |
| Lactose | 1% |
| Pyruvic acid | 0.1% |
| Tween 80 | 0.1% |
| Magnesium sulfate | 0.0575% |
| Ferrous sulfate | 0.0034% |
| Manganese sulfate | 0.012% |

The above-described composition was dissolved in distilled water. An acid such as acetic acid was added to adjust the pH of the solution to 3 to 5.5, followed by autoclave sterilization at 121° C. for 15 minutes.

As a result of investigation on the pH of the acid treatment solution, it was found that the pH set at 3.8 or greater enabled measurement of the number of surviving bacteria after treatment for 1 to 30 minutes. The acid treatment solution having a pH of 3.8 was therefore employed.

To 10 mL of the acid treatment solution having a pH 3.8, 1 mL of each of the three samples used in Example 1 was added, followed by incubation at 37° C. During the treatment, sampling was conducted as needed and the number of living bacteria was counted. The death velocity was determined based on the data thus obtained. The results are as shown below.

TABLE 2

| | Strain | | |
|---|---|---|---|
| | A | B | C |
| Death velocity during acid treatment (logarithm of the number of bacteria killed per minute) | 0.55 | 0.38 | 0.51 |

The above-described results show that the strain B is excellent in the death speed by the acid treatment, which, however, does not coincide with the order of Example 1 in the number of bacteria recovered after actual administration.

Example 3

In the next place, tolerance to bile treatment was compared assuming that the bacteria reached the intestines. As a treatment solution, that having the below-described composition and added with Oxgall was judged appropriate, when the treatment time and measurability of the number of bacteria were taken into consideration as in the case of the acid treatment.

Composition of Bile Treatment Solution

| | |
|---|---|
| Trypticase peptone (BBL) | 1% |
| Yeast extract (Difco) | 0.5% |
| Triptose (Difco) | 0.3% |
| Disodium hydrogen phosphate 12 hydrate | 2.03% |
| Sodium dihydrogen phosphate 2 hydrate | 0.156% |
| Diammonium citrate | 0.2% |
| Cysteine hydrochloride | 0.05% |
| Lactose | 1% |
| Pyruvic acid | 0.1% |
| Tween 80 | 0.1% |
| Magnesium sulfate | 0.0575% |
| Ferrous sulfate | 0.0034% |
| Manganese sulfate | 0.012% |

The above-described composition was dissolved in distilled water. To the resulting solution was added 0.1 to 5% of Oxgall (Difco) to dissolve the latter. in the former. The solution was adjusted to pH 8.0 with a sodium hydroxide solution, followed by autoclave sterilization at 121° C. for 15 minutes.

As a result of investigation on the concentration of Oxgall, it was found that the Oxgall concentration set at 1% or less enabled measurement of the number of surviving bacteria after the treatment for 1 to 30 minutes. The bile treatment solution having an Oxgall concentration of 1% was therefore employed. To 10 mL of the bile treatment solution containing 1% Oxgall, 1 mL of each of the three samples used in Example 1 was added, followed by treatment at 37° C. for 30 minutes. After the treatment, the number of living bacteria was counted. The bacterial viability after the bile treatment was measured based on the data thus obtained. The results are as shown below.

TABLE 3

| | Strain | | |
|---|---|---|---|
| | A | B | C |
| Bacterial viability (%) after bile treatment | <0.1 | 60 | 30 |

It has been found that the strain B exhibited the highest tolerance to bile, which was however different from the actual recovery results.

Example 4

Also in vitro, acid treatment and bile treatment were conducted successively in consideration that when the food passes through the digestive tracts, it passes successively through the stomach and intestines. In these successive treatments with an acid and bile, adjustment of an acid treatment solution to pH 4.3 or greater and a bile treatment solution to have an Oxgall concentration of 1% enabled measurement of the number of surviving bacteria after treatment. Described specifically, the successive treatments with an acid and bile as described below were performed.

To 10 mL of an acid treatment solution adjusted to pH 4.3 with acetic acid was added 1 mL of the syrup-containing fermented milk as employed in Example 1, followed by treatment at 37° C. for 30 minutes. Immediately after the treatment, 1 mL of the acid treated solution was added to a bile treatment solution containing 1% of Oxgall, followed by treatment at 37° C. for 30 minutes. A survival ratio of bacteria after the successive treatments with an acid and bile was compared among three strains.

TABLE 4

| | Strain | | |
|---|---|---|---|
| | A | B | C |
| Survival ratio (%) after successive treatments | <1 | 3 | 10 |

According to the assessment results, the bacterial viability after the successive treatments coincided with the actual recovery results of Example 1. In other words, the survival ratio of the strain B was the highest in the case of single treatment with an acid or bile, while that of the strain C was the highest after the successive treatments with an acid and bile, which coincided with the results of the actual recovery. This suggests that recovery of bacteria administered through a drink can be forecast based on the results of the in vitro successive treatments.

Example 5

The assessment by the above-described successive treatments was performed using a bred strain *B. breve* NE strain (strain D) to which bile tolerance had been imparted by the below-described method.

First, the *B. breve* A strain used as a base was subjected to mutation. A 50 mM phosphate buffer (pH 7.0) containing 5 μg/mL of NTG and the washed bacteria of *B. breve* were mixed at a ratio of 1:1. After treatment at 37° C. for 30 minutes, the mixture was washed twice with a phosphate buffer (pH 7.0). A nutrient medium was then inoculated with 1% of the resulting bacteria, followed by incubation at 37° C. for 16 hours.

The resulting NTG-treated bacteria were subjected to EMS treatment. A 50 mM phosphate buffer (pH 7.0) containing 0.4% of EMS and the above-described cultured bacteria were mixed at a ratio of 1:1. After treatment at 37° C. for 30 minutes, the mixture was washed twice with a phosphate buffer (pH 7.0). A nutrient medium was inoculated with 1% of the resulting bacteria, followed by culturing at 37° C. for 16 hours.

By using the resulting bacteria as an initial seed (added with 0.03% yeast extract), a seed culture was prepared. It was inoculated into a 18% whole milk medium sterilized at 100° C. for 90 minutes and cultured at 34° C. for about 20 hours, whereby a fermented milk was prepared. A glucose-fructose syrup was added to the milk to give a final concentration of 8%. The resulting mixture was dispensed into a glass container. After sealing with a rubber stopper, the container was stored at 10° C. for 10 days. Then, 10 mL of the sample after storage was added to 100 mL of a bile treatment solution having the composition as described in Example 4 and containing 2% of Oxgall. After bile treatment at 37° C. for 30 minutes, the solution was centrifuged at 5000×g for 10 minutes to recover the bacteria. The resulting bacteria were smeared on an agar plate. From the culture thus obtained, several single-colony-derived strains were selected and the strain D having improved tolerance were obtained.

By using the resulting strain and the strain C, syrup-containing fermented milks were prepared as in Example 1. In a similar manner to that employed in Example 4, the tolerance to successive treatments with an acid and bile was compared between these samples which had been stored at 10° C. for 7 days. The results are shown below.

TABLE 5

| | (cfu/mL) Strain | |
|---|---|---|
| | D | C |
| The original number of bacteria | $2.1 \times 10^8$ | $5.3 \times 10^8$ |
| The number of surviving bacteria after successive treatments | $3.7 \times 10^7$ | $9.3 \times 10^7$ |
| Survival ratio | 18% | 18% |

At the same time, drinking test was performed on these samples. Twelve healthy adult volunteers were divided into two groups and were asked to take 100 mL/day of each of the two syrup-containing fermented milks prepared in Example 5 for 3 days. On the next day after completion of the drinking, feces were collected and diluted stepwise with an anaerobic dilution water. From the number of colonies appearing on the selective plate, the number of bacteria thus recovered was calculated. A T-CBPC plate was used for *B. breve* D strain, while a T-LCM plate was used for *B. bifidum* C strain. The results are shown below.

TABLE 6

| | Strain | |
|---|---|---|
| | D | C |
| The number of bacteria recovered (logarithm) | 6.26 | 6.44 |

It has been found from these results that the strain D bred while subjecting it to single treatment with bile exhibited a survival ratio less than 20% after successive treatments with an acid and bile and the number of bacteria recovered after administration through drinking did not reach $1\times10^7$.

Example 6

Since it has been found that there is a high possibility that tolerance assessed by means of the successive treatments correlates with recovery of bacteria after administration through drinking, a strain was bred while subjecting it to the successive treatments and the resulting strain having tolerance was studied as to recovery of bacteria after administration through drinking.

A seed culture prepared using the strain A as a base was inoculated into a 20% whole milk medium (added with 0.03% yeast extract) UHT-sterilized at 135° C. for 3.5 seconds, followed by incubation at 34° C. for about 20 hours, whereby a fermented milk was obtained. Palatinose was then added to the milk to give a final concentration of 10%. The resulting mixture was dispensed in a glass container. While the container was sealed with a rubber stopper to block the air from entering the container, it was stored at 10° C. for 11 days. To 10 mL of the sample after storage was added 100 mL of an acid treatment solution having a composition as shown in Example 4 and having a pH adjusted to 4.3. Immediately after the resulting mixture was treated at 37° C. for 30 minutes, 10 mL of the treated solution was added to a bile treatment solution containing 1% of Oxgall. The mixture was treated at 37° C. for 30 minutes and then, centrifuged at 5640×g for 10 minutes to recover the bacteria. The resulting bacteria were smeared on an agar plate. From the culture thus obtained, several single-colony derived strains were selected, whereby *B. breve* YIT 4125 strain (which may hereinafter be called "4125 strain") and YIT 4126 strain (which may hereinafter be called "4126 strain") having improved tolerance to an acid and bile were obtained.

By using these strains and the strain A, syrup-containing fermented milks were prepared in a similar manner to that described in the beginning of Example 6. After storage at 10° C. for 7 days, the number of surviving bacteria after the successive treatments with an acid and bile was determined in a similar manner to that employed in Example 4.

The drinking test was performed also on these samples. Ten healthy male adult volunteers were divided into two groups and were asked to take, for 3 days, 100 mL/day of either one of a sample prepared using the 4125 strain or the strain A. Feces on the next day after completion of the drinking were collected and the extent of the recovery of the administered bacteria was measured using a T-CBP plate. After an interval of 1 week, the volunteers of each group were asked to take a sample different from the first one and the number of bacteria recovered was counted. An average of the results of the measurements conducted twice for each strain was designated as the number of bacteria recovered.

Table 7 shows the results of a survival ratio after the successive treatments with an acid and bile and results of recovery of bacteria administered through drinking, each on Day 7 after the storage of the fermented milk; and a change ratio in the number of living bacteria in the fermented milk product during 7 day storage. The "change rate" as used herein means the number of living bacteria, in terms of logarithm, which decreased per day during low-temperature storage.

TABLE 7

| | Strain | | |
|---|---|---|---|
| | A | 4125 Strain | 4126 Strain |
| Initial number of bacteria | $3.7 \times 10^8$ | $3.3 \times 10^8$ | $3.7 \times 10^8$ |
| The number of surviving bacteria after successive treatments | $7.8 \times 10^5$ | $1.3 \times 10^8$ | $2.1 \times 10^8$ |
| Survival ratio | 0.2% | 39.4% | 56.8% |

The number of bacteria recovered

| | Strain | | |
|---|---|---|---|
| | A | 4125 Strain | 4126 Strain |
| The number of bacteria recovered (logarithm) | 6.4 | 7.0 | Not test |

Change rate of the number of living bacteria in the product

| | Strain | |
|---|---|---|
| | A | 4125 Strain |
| Change rate of the number of living bacteria per day | 0.22 | 0.05 |

The 4125 and 4126 strains obtained in the present Example exhibited tolerance of 20% or greater to an acid and bile. The number of bacteria recovered when the 4125 strain was administered through drinking was $1\times10^7$ cfu/mL or greater.

A change rate of the number of living bacteria during the storage of the product was small, suggesting that the number of bacteria was kept high.

From the above-described results, it has been found that when the survival ratio after successive treatments with an acid and bile is 20% or greater, the number of bacteria recovered after administration of them through drinking becomes $10^7$ cfu/mL.

A storage test at 10° C. was then performed for three weeks on the above-described samples. A survival ratio of bacteria in the product after storage for 3 weeks is shown in Table 8.

TABLE 8

| | Strain | |
|---|---|---|
| | A | 4125 Strain |
| Survival ratio after 3 weeks | 21.0% | 69.6% |

A survival ratio of the bacteria in the product obtained using the 4125 strain was high even after storage for 3 weeks.

Example 7

A commercially available product was next investigated. Tolerance to an acid and bile of each of a commercially-available *Bifidobacterium*-bacteria- and syrup-containing fermented milk (Fermented milk E) and the fermented milk of Example 6 prepared using the 4125 strain (each fermented milk was stored for 7 days) was measured as in Example 4.

At the same time, one healthy adult volunteer was asked to take these products after lunch at an interval of one week and the number of *Bifidobacterium* bacteria derived from each product and contained in the feces on the next day was counted. The number of *Bifidobacterium* bacteria derived from the product was calculated as follows: first by selectively breeding only *Bifidobacterium* bacteria in the feces on a TOS plate (prepared in a similar manner to the T-CBPC plate of Example 1 except for the omission of an antibiotic), identifying, from them, the product-derived *Bifidobacterium* bacteria by Random Amplified Polymorphic DNA Fingerprinting (RAPD method) and calculating the number of recovered bacteria based on their existing proportion. The results are shown in Table 9.

TABLE 9

| | Product | |
|---|---|---|
| | Commercially available product E | 4125 Strain |
| The initial number of bacteria | $5.2 \times 10^7$ | $1.7 \times 10^8$ |
| The number of surviving bacteria after successive treatments with an acid and bile | $8.5 \times 10^6$ | $7.3 \times 10^7$ |
| Survival ratio | 16.3% | 42.9% |

The number of bacteria recovered

| | Strain | |
|---|---|---|
| | E | 4125 Strain |
| The number of bacteria recovered (logarithm) | <6.89 | 7.20 |

With regards to the commercially available syrup-containing fermented milk, a survival ratio of bacteria after successive treatments with an acid and bile was less than 20% and the recovery ratio of bacteria after administration through drinking did not reach $1\times10^7$ cfu/mL.

INDUSTRIAL APPLICABILITY

The present invention makes it possible to conveniently and accurately assess the extent to which *Bifidobacterium* bacteria in a fermented milk food reach the intestines.

The present invention also makes it possible to provide *Bifidobacterium*-bacteria-containing fermented milk food and drink permitting the high extent to which the bacteria reach the intestines even after storage.

The invention claimed is:

1. An isolated *Bifidobacterium breve* strain exhibiting viability of 20% or greater after treatment in an acid treatment solution at pH 4.3 at 37° C. for 30 minutes, followed by treatment in a bile treatment solution containing 1% bile at 37° C. for 30 minutes compared to the same strain prior to said acid and bile treatments.

2. The *Bifidobacterium breve* strain of claim 1, which is *Bifidobacterium breve* YIT strain 4125 (FERM BP-7813).

3. The *Bifidobacterium breve* strain of claim 1, which is *Bifidobacterium breve* YIT strain 4126 (FERM BP-7814).

4. A fermented food or drink which has been fermented by, and contains, the *Bifidobacterium breve* strain of claim 1.

5. The fermented food or drink of claim 4 which is a fermented milk product.

6. The fermented food or drink of claim 4 which contains saccharide-containing syrup.

7. A method for providing viable *Bifidobacterium breve* to the intestine of a subject, comprising orally administering the food or drink of claim 4 to said subject.

8. The *Bifidobacterium breve* strain of claim 1 that after storage for 7 days at 10° C., and after oral ingestion by a human, is recovered from the human intestines at a titer of $1\times10^7$ cfu/ml or more.

9. A method for making a *Bifidobacterium breve* strain that has increased viability after refrigerated storage comprising:

treating a *Bifidobacterium breve* strain in an acid treatment solution at pH 4.3 at 37° C. for 30 minutes, treating said *Bifidobacterium breve* strain in a bile treatment solution containing 1% bile at 37° C. for 30 minutes, isolating a single-colony derived *Bifidobacterium breve* strain that maintains a viability of 20% or more after treatment with acid and bile under the conditions stated above, compared to the viability of the same strain that has not been treated with bile and acid.

* * * * *